(12) United States Patent
Hu et al.

(10) Patent No.: US 12,150,626 B2
(45) Date of Patent: Nov. 26, 2024

(54) LARYNGOSCOPE

(71) Applicant: SZ HUGEMED MED TECH DEV CO., LTD, Guangdong (CN)

(72) Inventors: Jifan Hu, Guangdong (CN); Yuesong Zhang, Guangdong (CN)

(73) Assignee: SZ HUGEMED MED TECH DEV CO., LTD, Guangdong (CN)

( * ) Notice: Subject to any disclaimer, the term of this patent is extended or adjusted under 35 U.S.C. 154(b) by 692 days.

(21) Appl. No.: 17/420,580

(22) PCT Filed: Apr. 24, 2020

(86) PCT No.: PCT/CN2020/086637
§ 371 (c)(1),
(2) Date: Jul. 2, 2021

(87) PCT Pub. No.: WO2021/036307
PCT Pub. Date: Mar. 4, 2021

(65) Prior Publication Data
US 2022/0104698 A1    Apr. 7, 2022

(30) Foreign Application Priority Data

Aug. 23, 2019  (CN) .......................... 201910785818.1

(51) Int. Cl.
*A61B 1/00* (2006.01)
*A61B 1/05* (2006.01)
(Continued)

(52) U.S. Cl.
CPC .......... *A61B 1/267* (2013.01); *A61B 1/00052* (2013.01); *A61B 1/05* (2013.01); *A61B 1/0676* (2013.01)

(58) Field of Classification Search
CPC . A61B 1/2673; A61B 1/2676; A61B 1/00066; A61B 1/00; A61B 1/05;
(Continued)

(56) References Cited

U.S. PATENT DOCUMENTS 4,579,108 A   4/1986  Bauman
4,979,499 A   12/1990 Sun
(Continued)

FOREIGN PATENT DOCUMENTS

CN    101238969 A    8/2008
CN    201977766 U    9/2011
(Continued)

OTHER PUBLICATIONS

International Search Report issued to International Application No. PCT/CN2020/086637 dated Jun. 30, 2020.
(Continued)

*Primary Examiner* — Ellen C Hammond
*Assistant Examiner* — Holly Joanna Lane
(74) *Attorney, Agent, or Firm* — McNees Wallace & Nurick LLC

(57) ABSTRACT

Provided is a laryngoscope that includes a display screen, a handle connected to the display screen, a lens connected to the handle, and a housing portion that is sleeved on the lens and the handle and fitted with the handle. The housing portion includes a housing and a transparent cover fastened with the housing. The lens is inserted into the housing and a shooting portion of the lens is exposed out of the housing. The transparent cover covers the shooting portion of the lens and is sealingly fastened with the housing.

4 Claims, 3 Drawing Sheets

(51) Int. Cl.
*A61B 1/06* (2006.01)
*A61B 1/267* (2006.01)

(58) Field of Classification Search
CPC ....... A61B 1/267; A61B 1/24; A61B 1/00684; A61B 1/07
See application file for complete search history.

(56) References Cited

U.S. PATENT DOCUMENTS

| | | | | |
|---|---|---|---|---|
| 8,202,215 | B2* | 6/2012 | Xiao | A61M 16/0488 600/185 |
| 2006/0020166 | A1* | 1/2006 | Berall | A61B 1/00142 600/186 |
| 2010/0261967 | A1* | 10/2010 | Pacey | A61M 16/0495 600/188 |
| 2011/0028790 | A1 | 2/2011 | Farr et al. | |
| 2011/0130632 | A1* | 6/2011 | McGrail | G02B 23/2446 600/188 |
| 2011/0270038 | A1* | 11/2011 | Jiang | A61B 1/00073 600/188 |
| 2014/0160261 | A1* | 6/2014 | Miller | A61B 1/05 348/77 |
| 2014/0336466 | A1* | 11/2014 | Young | A61B 1/06 600/188 |
| 2016/0206188 | A1* | 7/2016 | Hruska | A61B 1/0684 |
| 2016/0256047 | A1 | 9/2016 | Newcomb et al. | |
| 2018/0206705 | A1* | 7/2018 | Chan | A61B 1/267 |
| 2019/0133430 | A1* | 5/2019 | Inglis | A61B 1/00052 |

FOREIGN PATENT DOCUMENTS

| | | |
|---|---|---|
| CN | 102481429 A | 5/2012 |
| CN | 202313228 U | 7/2012 |
| CN | 102984994 A | 3/2013 |
| CN | 103298391 A | 9/2013 |
| CN | 204839429 U | 12/2015 |
| CN | 105286771 A | 2/2016 |
| CN | 105595952 A | 5/2016 |
| CN | 106419811 A | 2/2017 |
| CN | 107072482 A | 8/2017 |
| CN | 109497924 A | 3/2019 |
| CN | 208837903 U | 5/2019 |
| CN | 209074543 U | 7/2019 |
| CN | 110338744 A | 10/2019 |
| CN | 211066525 U | 7/2020 |

OTHER PUBLICATIONS

Search Report issued to European counterpart Application No. 20858890.5 dated Jul. 7, 2022.

\* cited by examiner

LARYNGOSCOPE

CROSS-REFERENCE TO RELATED APPLICATIONS

This application is a U.S. National Phase Application of co-pending International Patent Application number PCT/CN2020/086637 filed on Apr. 24, 2020, which claims priority to Chinese patent applications No. 201910785818.1 filed on Aug. 23, 2019, disclosure of which is disclosures of which are incorporated herein by reference in its entirety-their entireties.

TECHNICAL FIELD

The present application relates to the technical field of medical devices, for example, relates to a laryngoscope.

BACKGROUND

A lens that allows light to transmit through for a camera is typically provided at the front end of a housing of a lens portion of a laryngoscope. Such structured lenses however are mostly thick, and sometimes they may not be firmly mounted causing them to shake during use, and they are inconvenient for maintenance. In addition, because the lens is thick, the lens has unsatisfactory light transmittance, and so the lens is easy to reflect light during use when being shone by light adding lamps placed around the camera, affecting the camera's shooting effect.

SUMMARY

The present application provides a laryngoscope having a stable and reliable structure, effectively improving the shooting definition of a laryngoscope. Furthermore, disassembly and assembly, as well as maintained of the laryngoscope is facilitated.

A laryngoscope is provided and includes a display screen, a handle connected to the display screen, a lens connected to the handle, and a housing portion sleeved on the lens and the handle and fitted with the handle; where the housing portion includes a housing and a transparent cover fastened with the housing; and the lens is inserted into the housing and a shooting portion of the lens is exposed out of the housing, and the transparent cover covers the shooting portion of the lens and is sealingly fastened to the housing.

The lens includes a lens body and a tongue depressor extending from the lens body in a direction away from the handle, and the shooting portion is disposed at an end of the lens body far away from the handle.

The lens body and the tongue depressor are integrally formed in a bent shape.

The shooting portion includes a camera and a light adding lamp which are embedded at the end of the lens body far away from the handle, and the camera and the light adding lamp are electrically connected to an electric control device disposed in the lens body.

The housing includes a first housing body sleeved on the handle and the lens body and adjacent to a periphery of a first portion of the handle, and a second housing body extending from the first housing body and sleeved on a periphery of a second portion of the lens body 3 far away from the handle, and the tongue depressor is inserted into the second housing body.

The second housing body is provided with an elongated groove configured for exposing the shooting portion out of the second housing body, and the transparent cover covers the shooting portion and is sealingly fastened with peripheral edges of the elongated groove.

The transparent cover is formed by a flexible transparent film covering on the shooting portion.

A side wall of the first housing body is provided with a observation window.

An edge of a port of the first housing body is provided with a catch, an end of the handle far away from the lens is provided with a hook, and the catch is interlocked with the hook of the handle.

DETAILED DESCRIPTION

Technical solutions of the present application are further described below through embodiments in conjunction with the drawings.

Figure 1:
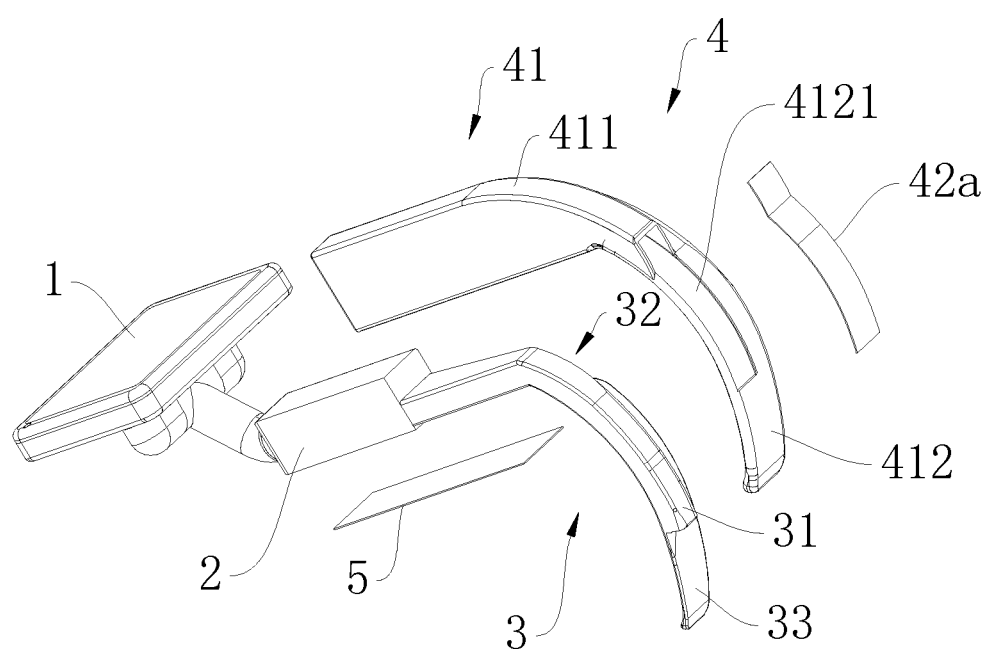
FIG. 1 is a first exploded diagram of a laryngoscope according to an embodiment of the present disclosure.
Figure 2:
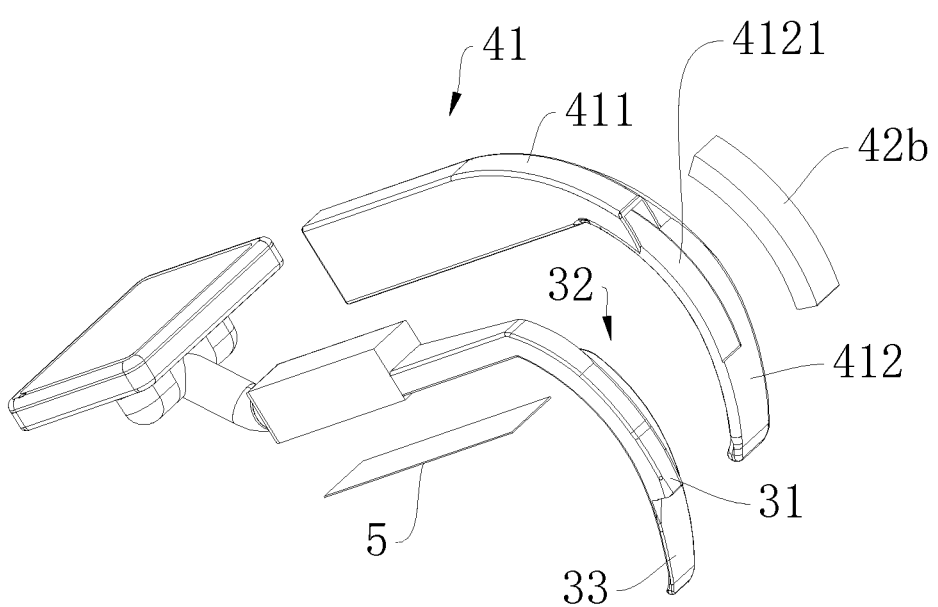
FIG. 2 is a second exploded diagram of a laryngoscope according to an embodiment of the present disclosure.
Figure 3:
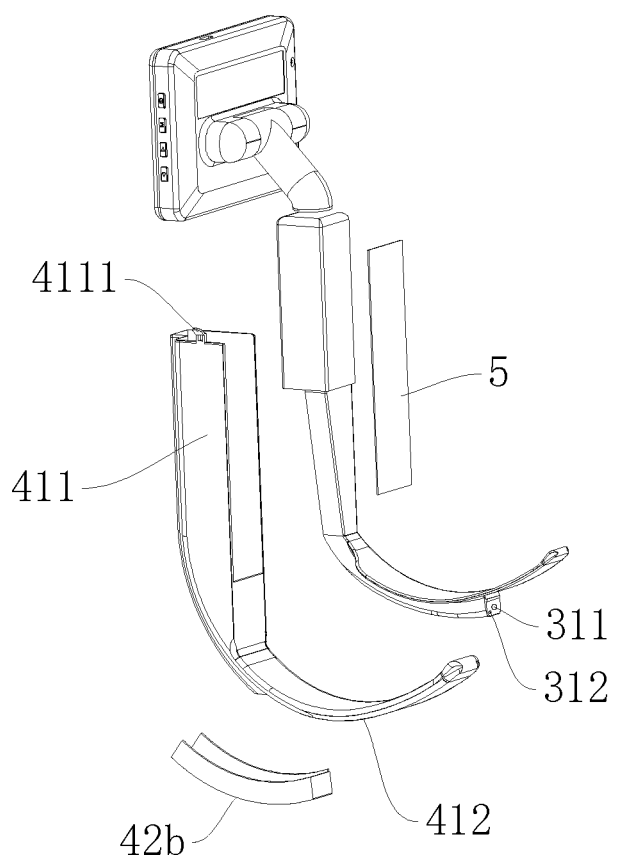
FIG. 3 is a third exploded diagram of a laryngoscope according to an embodiment of the present disclosure.

As illustrated in FIGS. 1 to 3, a laryngoscope is provided and includes a display screen 1, a handle 2 connected to the display screen 1, a lens 3 connected to the handle 2, and a housing portion 4 sleeved on the lens 3 and the handle 2 and fitted with the handle 2. The housing portion 4 includes a housing 41 and a transparent cover 42b fastened with the housing 41, the lens 3 is inserted into the housing 41 and a shooting portion 31 of the lens 3 is exposed out of the housing 41, and the transparent cover 42b covers the shooting portion 31 of the lens 3 and is sealed and is sealingly fastened to the housing 41. To facilitate the disassembly and assembly with the housing portion 4, the display screen 1, the handle 2 and the lens 3 in the embodiment can be pre-assembled into a whole, and then be inserted into the cavity of the housing portion 4. As the transparent cover 42b is sealingly connected to the housing 41, many problems caused by the use of lenses in traditional laryngoscopes can be avoided.

In the embodiment, the lens 3 includes a lens body 32 and a tongue depressor 33 extending from the lens body 32 in a direction away from the handle 2, and the lens body 32 and the tongue depressor 33 are integrally formed in a bent shape. The shooting portion 31 is disposed at an end of the lens body 32 far away from the handle 2, the shooting portion 31 includes a camera 311 and a light adding lamp 312 which are embedded at the end of the lens body 32 far away from the handle 2, where the camera 311 and the light adding lamp 312 are electrically connected to an electric control device disposed in the lens body 32. The specific structural connection and the design of the electric control device in this part are similar to the structure and principle of a traditional laryngoscope and are common in the related art, and details are not repeated here.

The housing 41 of the embodiment includes a first housing body 411 sleeved on the handle 2 and the lens body 32 and adjacent to a periphery of the first portion of the handle 2, and a second housing body 412 extending from the first housing body 411 and sleeved on the periphery of the second portion of the lens body 32 far away from the handle 2. The tongue depressor 33 is inserted into the second housing body 412. To facilitate the shooting of the camera 311 and the light adding lamp 312 in the shooting portion 31 through the transparent cover 42b and to facilitate the mounting of the transparent cover 42b, in the embodiment, the second housing body 412 is provided with an elongated groove 4121 configured for the shooting portion 31 to be exposed out of the second housing body 412, and the transparent cover 42b covers the shooting portion 31 and is sealingly fastened with peripheral edges of the elongated groove 4121.

The transparent cover 42b of the embodiment may be formed by a flexible transparent film 42a (shown in FIG. 1) covering on the shooting portion 31, and the flexible transparent film 42a may be provided as a plastic film made of PP. During mounting, the pre-cut plastic film is configured to cover the position of the elongated groove 4121 through processes such as laser welding, epoxy resin bonding or ultrasonic welding, etc. and be sealingly connected to the housing 41, and then the end of the lens 3 provided with the tongue depressor 33 is inserted into the housing 41. When the shooting portion 31 of the lens 3 is mounted in place, the preset plastic film can be jacked up so as to be covering on the outer side of the shooting portion 31 and be consistent with the appearance of the shooting portion 31, that is, the shape of the preset plastic film changes from the shape of the flexible transparent film 42a in FIG. 1 into the shape of the transparent cover 42b in FIG. 2; therefore, the trouble caused by the traditional laryngoscopes adopting lenses is effectively avoided.

To facilitate the observation of the internal condition of the housing 41, a observation window is further provided at a side wall of the first housing body 411, and the observation window may be a transparent sheet 5 provided at a gap at the side wall of the first housing 411. In addition, to facilitate the disassembly and assembly of the housing 41, the edge of the port at the end of the first housing body 411 far away from the second housing body 412 is provided with a catch 4111, and the end of the handle 2 far away from the lens 3 is provided with a hook (not shown). The catch 4111 is interlocked with the hook of the handle 2, so that the housing portion 4 can be conveniently and flexibly removed, and the various portions can be conveniently cleaned and maintained.

By the fastening of the transparent cover with the housing, the laryngoscope provided by the present application can effectively avoid the abnormal shooting caused by the thick lens of the traditional laryngoscope or unstable installation, and can also facilitate the disassembly and assembly the housing portion from or with other portions, as well as the maintenance of the various portions.

What is claimed is:

1. A laryngoscope, comprising:
a display screen;
a handle, connected to the display screen;
a lens, connected to the handle; and
a housing portion sleeved on the lens and the handle and fitted with the handle;
wherein the housing portion comprises a housing and a transparent cover fastened with the housing; and the lens is inserted into the housing and a shooting portion of the lens is exposed out of the housing, and the transparent cover covers the shooting portion of the lens and is sealingly fastened to the housing;
wherein the lens comprises a lens body and a tongue depressor extending from the lens body in a direction away from the handle, and the shooting portion is disposed at an end of the lens body far away from the handle;
wherein the shooting portion comprises a camera and a light adding lamp which are embedded at the end of the lens body away from the handle, wherein the camera and the light adding lamp are electrically connected to an electric control device disposed in the lens body;
wherein the housing comprises a first housing body that is sleeved on the handle and the lens body and adjacent to a periphery of a first portion of the handle, and a second housing body extending from the first housing body and sleeved on a periphery of a second portion of the lens body 3 far away from the handle, and wherein the tongue depressor is inserted into the second housing body;
wherein a side wall of the second housing body is provided with an elongated groove configured for exposing the shooting portion out of the second housing body, and the transparent cover covers the shooting portion and is sealingly fastened with peripheral edges of the elongated groove to facilitate the shooting of the camera and the light adding lamp in the shooting portion through the transparent cover; and
wherein a side wall of the first housing body is provided with an observation window configured to facilitate observation of an internal condition of the housing.

2. The laryngoscope of claim 1, wherein the lens body and the tongue depressor are integrally formed in a bent shape.

3. The laryngoscope of claim 1, wherein the transparent cover is formed by a flexible transparent film covering on the shooting portion.

4. The laryngoscope of claim 1, wherein an edge of a port of the first housing body is provided with a catch, an end of the handle far away from the lens is provided with a hook, wherein the catch is interlocked with the hook of the handle.

* * * * *